United States Patent [19]

Dupré

[11] 4,351,754

[45] Sep. 28, 1982

[54] THICKENING AGENT FOR AQUEOUS COMPOSITIONS

[75] Inventor: Jean Dupré, Levittown, Pa.

[73] Assignee: Rohm and Haas Company, Philadelphia, Pa.

[21] Appl. No.: 139,053

[22] Filed: Apr. 10, 1980

Related U.S. Application Data

[63] Continuation-in-part of Ser. No. 75,860, Sep. 17, 1979, abandoned.

[51] Int. Cl.³ .................................................. C08K 3/36
[52] U.S. Cl. ..................................... 524/445; 526/313; 526/317; 524/446; 524/558
[58] Field of Search .................. 260/29.6 H, 29.6 TA, 260/29.6 RW; 526/313, 317, 318, 320

[56] References Cited

U.S. PATENT DOCUMENTS

| | | | |
|---|---|---|---|
| 3,652,497 | 3/1972 | Junas | 526/317 |
| 3,657,175 | 4/1972 | Zimmerman | 260/29.6 T |
| 3,779,970 | 12/1973 | Evani | 260/29.6 RW |
| 3,891,591 | 6/1975 | Chang | 260/29.6 WB |
| 3,894,980 | 7/1975 | DeTommaso | 260/29.6 TA |
| 3,960,935 | 6/1976 | Samour | 526/304 |
| 4,138,381 | 2/1979 | Chang | 260/29.6 TA |

Primary Examiner—Paul R. Michl
Attorney, Agent, or Firm—Jordan J. Driks

[57] ABSTRACT

A mixture of a water swellable clay mineral and an alkali soluble and thickenable (meth)acrylic acid emulsion copolymer provides a highly effective thickening and gelling agent for aqueous systems at low concentrations. The gels are self-supporting and have high strength and thus are particularly useful as air fresheners and other applications where firm gels are desirable. A synergistic thickening effect between the (meth)acrylic acid copolymer and the clay mineral is observed.

11 Claims, No Drawings

THICKENING AGENT FOR AQUEOUS COMPOSITIONS

BACKGROUND OF THE INVENTION

This is a continuation-in-part application of Ser. No. 075,860 filed Sept. 17, 1979 now abandoned, the latter application having been abandoned upon the filing of this application.

This invention relates to compositions for thickening aqueous systems, and more particularly to a mixture of a clay mineral and an acrylic or methacrylic acid emulsion copolymer which exhibits synergistic thickening activity and which forms self-supporting, firm, high strength gels.

This application is related to the following commonly assigned copending applications of C. J. Chang and T. E. Stevens, each for "(Meth)acrylic Acid Emulsion Copolymers for Thickening Purposes": Ser. No. 974,466 filed Dec. 29, 1978; a continuation-in-part application thereof, Ser. No. 075,862 filed Sept. 17, 1979; and a continuation-in-part application of Ser. No. 075,862, whose Ser. No. is 101,615, filed Dec. 10, 1979.

Thickeners are used in aqueous systems for a variety of reasons. The enhanced viscosity afforded by a thickener is often necessary in order to reduce flow and to maintain an active agent on a substrate. Typical compositions which utilize thickeners are hand lotions, pharmaceutical preparations, hand and industrial cleansers, and flowable agricultural pesticide formulations. The increased viscosity provided by the thickener may range from slight thickening in moderately flowable systems to generally immobile systems such as gels. In addition to viscosity improvement, many thickeners are pseudoplastic so that an aqueous composition containing the thickener may be blended with other ingredients by agitation. However, because many thickeners are expensive either to synthesize or to derive from natural materials, and because many thickeners exhibit incompatibility with other ingredients of aqueous systems or require such high levels as to render them unduly expensive, the search continues for new thickeners.

Particularly in the field of aqueous gels is there continual need for improvements in thickeners. For example, natural gums, such as gum carrageenan, require high levels to give high strength gels. Since natural gums initially are expensive, their required high use levels add further to the cost of their use in aqueous systems. Natural gums also exhibit variable performance from lot to lot and tend to exude water during freeze-thaw cycles (syneresis). Even the presently available synthetic water soluble polymers and inorganic thickeners (such as clay minerals) cannot provide high strength, self supporting gels. Moreover, the inorganic thickeners do not have the elasticity and plasticity sufficient to withstand the stresses of handling and shipping. In the latter case, aqueous gels based upon inorganic thickeners will crack or crumble as they begin to lose water.

SUMMARY OF THE INVENTION

In one aspect, the invention is a thickener composition which can be used to provide a wide range of thickening in aqueous systems, from a slow flowing liquid to a firm gel. In another aspect, the thickener composition, although pseudoplastic, does not exhibit a maximum viscosity and then reduce in viscosity as the amount in an aqueous system is increased, as contrasted, for example, with many known thickeners based upon synthetic ingredients and clay minerals as discussed in U.S. Pat. No. 4,087,365 and other technical literature. In still another aspect the thickener composition of the invention, particularly when used to form gels, can hold and immobilize at low concentrations large quantities of water and active ingredients dispersed therein. Thus, the thickener composition can be used as a highly efficient and economical absorbent as compared with presently known absorbents which depend upon high concentrations of synthetic polymers.

Briefly, the thickener composition of the invention is a mixture of (A) a water swellable clay mineral, and (B) an acrylic or methacrylic acid emulsion copolymer characterized by the inclusion of a hydrophobe containing monomer. The proportion of clay mineral and acrylic or methacrylic acid copolymer as well as the total amounts of the mixture in an aqueous system may vary widely, depending upon the degree of thickening desired and other properties, such as the strength, elasticity and plasticity of the gelatinous form of aqueous systems prepared with the thickener composition.

Unless the context clearly indicates otherwise, the term "acrylic" in the following discussion includes both acrylic and methacrylic acids, esters and polymers, and the term "(meth)acrylic" means, optionally, an acrylic or methacrylic acid, ester or polymer.

Although mixtures of acrylic polymers with clay minerals as thickeners or viscosifiers for aqueous systems are generally known, and the use of the (meth)acrylic acid copolymer component of the present invention is the subject of the copending applications cited above, the composition of the present invention exhibits an unexpectedly high level of thickening, even synergistic thickening, while avoiding many of the deficiencies of known thickeners described above. Representative of the prior art describing thickeners based upon a mixture of clay minerals and synthetic polymers is U.S. Pat. No. 3,976,580 describing the combination of polyacrylamide and bentonite in water to form gels for fire extinguishing; U.S. Pat. No. 4,060,678 describing cationic hydrogels useful for reaction or complexing with materials having an opposite charge such as agricultural chemicals, cosmetics, pharmaceuticals, and a variety of industrial chemicals; and numerous patents on drilling fluid compositions such as U.S. Pat. Nos. 3,323,603, 3,472,325, and the beneficiating of clays used in drilling fluids, such as U.S. Pat. Nos. 2,948,678, 3,687,846, 3,816,308, 3,838,047 and 4,087,365.

In summary, the thickener composition of the invention is useful for thickening a wide variety of aqueous systems, from low viscosity improvement to the formation of firm, high strength gels, without significant syneresis in the gel state and with an order of thickening efficiency (good thickening at low concentrations) providing economical thickening and the ability to control product quality from sample to sample. In addition, the thickener composition is easily solubilized (by neutralization of the emulsion copolymer component), can be readily shear thinned, and will thicken alkaline and electrolyte containing aqueous systems. The uses for the thickener composition therefore are virtually unlimited and include household uses such as gel air fresheners; personal uses such as lotions, creams and other cosmetic or toiletry applications, liquid cleansers, diapers, tampons and the like; and a host of industrial and agricultural applications, such as oil well drilling fluids, flowable agricultural pesticide formulations, seed coatings, potting soils, and soaking up industrial spills.

DETAILED DESCRIPTION

The clay mineral component of the thickener composition is a well known material and includes any clay mineral which is water swellable. Clay minerals are earthy or stony mineral aggregates consisting essentially of hydrous silicates of aluminum, iron and/or magnesium. Clay minerals may be amorphous and/or crystalline and may contain a variety of other (non-clay) minerals, such as quartz, calcite, feldspar and pyrites. Clay minerals useful in the invention swell and form colloidal dispersions when hydrated and this condition is reversible when the material loses its water, short of the state of fusion. The preferred clay minerals are those of the montmorillonite group, including beidellite, bentonite, hectorite, montmorillonite itself, nontronite and saponite. Most well known of the bentonite species are sodium bentonite, also known as Wyoming bentonite, and calcium bentonite. Although the latter has negligible swellability, it can be converted in a known manner to the swellable type by addition of a sodium alkali such as sodium carbonate to exchange calcium ions for sodium ions. Where the thickener composition is intended to be flowable, the clay mineral component should have small particle size, of the order of about 50 microns or less, preferably an average particle size less than about 20 microns. However, particle size is not critical and may be varied as desired to obtain the requisite flowability. A variety of other clay minerals may be used in combination with those of the montmorillonite group. For example, metabentonite is considered to be a mixture of one or more members of the illite group of clay minerals and montmorillonite. The foregoing and other clay minerals are described in the literature together with properties and uses, as in Kirk-Othmer, Encyclopedia of Chemical Technology, Second Edition, Interscience Publishers (1964), Volume 5, pages 541-586, and Lange's Handbook of Chemistry, 10th Edition, McGraw-Hill Book Company (1967), pages 220-223, both being incorporated herein by reference.

The (meth)acrylic acid copolymer component of the thickener composition is described in the above-identified application Ser. No. 974,466 and the continuation-in-part applications thereof (each incorporated herein by reference). However, for the sake of convenience the following summarizes the character of this copolymer.

The copolymer component is a water insoluble emulsion copolymer of:

(1) acrylic or methacrylic acid (abbreviated "AA" and "MAA," respectively, hereinbelow);

(2) a (meth)acrylic acid ester of a ($C_8$–$C_{24}$) alkyl monoether of a polyethylene glycol having at least two oxyethylene units therein, of the formula (I): $H_2C=C(R)-C(O)-O-(CH_2-CH_2O)_n-R^o$ wherein R is H or $CH_3$, the latter being preferred, n is at least 2, and preferably has an average value of at least 10, up to 40 to 60 or even up to 70 or more, and $R^o$ is a hydrophobic group containing at least 8 carbon atoms, e.g., about 8-24 carbon atoms, preferably 12 to 18 carbon atoms or having an average of 12 to 18 or more carbon atoms;

(3) a ($C_1$–$C_4$)alkyl (meth)acrylate, preferably ethyl acrylate (abbreviated "EA" hereinbelow); and (4) optionally, a minor amount, effective for cross-linking, of a polyethylenically unsaturated monomer.

The copolymer component is further characterizable as an alkali soluble and alkali thickenable material meaning, for the purposes of this specification, that addition of an alkali to an aqueous dispersion containing the water insoluble emulsion copolymer (in an amount to at least partially neutralize the copolymer) will dissolve the copolymer and simultaneously cause the copolymer to swell and thereby to thicken the dispersion, in the manner described in British Pat. No. 870,994.

The copolymer should have a weight average molecular weight of about 100,000 to several million and therefore is prepared by emulsion polymerization to a solids content of about 25 to 50% by weight. If it is desired to obtain molecular weights in the lower part of the range or even down to about 80,000 weight average molecular weight, a chain-transfer agent may be used. Monomer component (4) serves to provide molecular weights in the higher portion of the range and provides light cross-linking. The monomer components (1) to (4) above may be used, respectively, in the ranges of (1) 20-50 weight percent, (2) 0.5 to 25 weight percent, (3) at least 30 weight percent, and (4), when present, about 0.05 percent to about 1.0 percent, the percentages of all monomers totaling 100 percent. Preferred ranges are (1) 35-45 weight percent, (2) 1-15 weight percent, and (3) 40-60 weight percent, respectively.

Typically, $R^o$ may be alkyl ($C_8$–$C_{24}$), aralkyl or the residue of a polycyclic hydrocarbyl compound such as lanolin or cholesterol. Alkyl groups include lauryl, tridecyl, myristyl, pentadecyl, cetyl, palmityl, stearyl and eicosyl. Mixtures may also be used, such as alkyl groups resulting from the ethoxylation of mixtures of lauryl, stearyl, cetyl and palmityl alcohols. Aralkyl groups include alkylphenyl groups such as octylphenyl and nonylphenyl.

Tables A and B below list a variety of monomers of formula I useful in preparing the emulsion copolymer component of the clay mineral/emulsion copolymer mixtures of the invention. Table A lists 19 methacrylate monomers (Nos. 1-19) prepared from methacrylic acid and the indicated alkyl monoether of polyethylene glycol. Table A also lists 19 acrylate monomers (Nos. 21-39) made from acrylic acid and alkyl, alkaryl or polycyclic hydrocarbyl monoethers of polyethylene glycol. Table B lists various methacrylate monomers (Nos. 41-52) prepared from methacrylic acid and the indicated alkyl poly(ethyleneoxy) ethanol or alkylphenoxypoly (ethyleneoxy) ethanol. In both Tables, n is the number of ethyleneoxy (EO) units in the ester groups. Methods suitable for preparing the monomers of Tables A and B are described in the above-identified application Ser. No. 101,615 filed Dec. 10, 1979 and the parent applications thereof.

TABLE A

| Monomer No. | | Alkyl Monoether of Polyethylene Glycol | |
|---|---|---|---|
| Methacrylate | Acrylate | $R^o$ Group | n (no. of EO Units) |
| 1 | 21 | Lauryl ($C_{12}$)* | 4 |
| 2 | 22 | Lauryl ($C_{12}$)* | 23 |
| 3 | 23 | ($C_{14}$–$C_{18}$)** | 20 |
| 4 | 24 | ($C_{14}$–$C_{18}$)** | 30 |
| 5 | 25 | ($C_{14}$–$C_{18}$)** | 40 |
| 6 | 26 | Stearyl ($C_{18}$) | 2 |
| 7 | 27 | Stearyl ($C_{18}$) | 10 |
| 8 | 28 | Stearyl ($C_{18}$) | 20 |
| 9 | 29 | ($C_{20}$–$C_{24}$)*** | 20 |
| 10 | 30 | ($C_{20}$–$C_{24}$)*** | 60 |
| 11 | 31 | Stearyl ($C_{18}$) | 30 |
| 12 | 32 | Octylphenyl ($C_{14}$) | 16 |

TABLE A-continued

| Monomer No. | | Alkyl Monoether of Polyethylene Glycol | |
|---|---|---|---|
| Methacrylate | Acrylate | R⁰ Group | n (no. of EO Units) |
| 13 | 33 | Octylphenyl ($C_{14}$) | 30 |
| 14 | 34 | Octylphenyl ($C_{14}$) | 40 |
| 15 | 35 | n-tridecyl ($C_{13}$) | 13 |
| 16 | 36 | Iso-hexadecyl ($C_{16}$) | 20 |
| 17 | 37 | Lanolin ($C_{30}$) | 25 |
| 18 | 38 | Cholesterol ($C_{27}$) | 24 |
| 19 | 39 | Nonylphenol ($C_{15}$) | 15 |

*Mixture of about 65% n-dodecyl and about 35% n-tetradecyl
**Mixture of monoalkyl ethers (0–4% $C_{14}$, at least 60% $C_{18}$ and at least 23% $C_{16}$)
***Mixture of monoalkyl ethers (60% $C_{20}$, 20% $C_{22}$, 10% $C_{24}$, remaining 10% of higher chain length alkyl, e.g. $C_{25}$–$C_{30}$ and lower chain length alkyl, e.g. $C_{16}$–$C_{18}$).

TABLE B

| Methacrylate Monomer No. | Alkyloxy or Alkylphenoxypoly (ethyleneoxy)$_n$ ethanol | |
|---|---|---|
| | R⁰ Group | n(No. of EO Units) |
| 41 | n-Octyl | 30 |
| 42 | n-Decyl | 30 |
| 43 | n-Decyl | 50 |
| 44 | n-Dodecyl | 10 |
| 45 | n-Dodecyl | 20 |
| 46 | n-Dodecyl | 30 |
| 47* | n-Dodecyl/n-Tetradecyl | 23 |
| 48 | n-Tetradecyl | 30 |
| 49 | Octylphenyl | 30 |
| 50 | Nonylphenyl | 15 |
| 51 | n-Octadecyl | 20 |
| 52 | n-Tetradecyl | 0 |

*Mixture of about 65% n-dodecyl and about 35% n-tetradecyl.

Emulsion polymerization techniques for preparing polymers of the invention are well known. For example, the monomers may be polymerized in an aqueous dispersion containing an anionic surfactant such as sodium lauryl sulfate and a water soluble free radical initiator such as an alkali metal persulfate or ammonium persulfate. When molecular weights at the low end of the range are desired, there may be added to the polymerization systems small amounts of a chain transfer agent such as an alkyl mercaptan containing from about 4 to 22 carbon atoms. Since the lower molecular weight reduces thickening efficiency of the copolymer, it is preferred that it be omitted with respect to many uses of the present invention.

Monomer component (4) is any polyethylenically unsaturated monomer which is copolymerizable with monomer components (1), (2) and (3). Typical monomers include diallylphthalate, divinylbenzene, allylmethacrylate, and ethyleneglycol dimethacrylate.

The resulting polymers are highly branched or have the form of three dimensional networks. Upon at least partial neutralization the copolymer swells substantially to form a "micro-gel" structure, thus providing thickening properties.

The clay mineral and copolymer may be admixed in a variety of ways to provide the thickener or thickened compositions of the invention. For example, the components may be blended, while either or both are in aqueous dispersion or dry form, followed by addition of a neutralizing agent. Alternatively, the copolymer component may first be neutralized in aqueous dispersion form and then blended with the clay mineral. In either case, the blend is then added to the aqueous system to be thickened or additives are blended into the copolymer/clay mixture (before or after neutralization), to provide the end product. Preferably, the components are separately blended (as dry components or as dispersions or slurries) into an aqueous dispersion to be thickened, followed by the neutralization step. Although aqueous concentrates of the clay mineral and copolymer in acid form may be formed and added to an aqueous dispersion to be thickened as needed, followed by neutralization, such concentrates tend to be too viscous for easy handling. It is nevertheless possible to prepare either a dry blend or an aqueous, high solids composition which is sufficiently low in viscosity as to be pumpable or pourable, and then to further thicken the admixture by addition of an alkaline material.

The thickener composition may be provided in a dry state in a number of ways. For example, the unneutralized copolymer may be spray dried and blended with dry clay mineral. However, it is also possible to spray dry or otherwise dehydrate the neutralized thickener composition, alone or in admixture with the clay mineral, and then reconstitute the aqueous thickener dispersion at a future time and place by agitation in an aqueous medium, provided the pH of the dispersion is maintained at pH 7 or higher.

Any alkaline material suitable for raising the pH of an aqueous dispersion of ingredients A and B of the thickener composition to 7 or higher may be utilized. Suitable neutralizers are alkalis such as sodium potassium or lithium hydroxide, a volatile amine such as triethyl amine, or triethanol amine, or ammonium hydroxide, singly or in admixture. The neutralization may be carried out to a pH of as high as 13 if desired but no special benefit results from neutralizing beyond about 7. At least about 0.5 equivalents of the alkali for neutralizing the copolymer will be effective but more or less of the neutralizing agent may be used according to the thickening effect desired, since the relationship between the degree of neutralization and the viscosity increase is generally linear.

The proportions of clay mineral component A and copolymer component B are not critical and may be varied for the thickening and solubilization desired for the intended end use. Generally, greater thickening occurs upon increases in the amount of copolymer than will result upon increases in the amount of clay mineral and the mixture will become gelatinous above about 100,000 cps. viscosity (Brookfield Viscometer, 75° F., 0.5 rpm). From the standpoint of good economy, low concentrations of thickener in the final aqueous dispersions are preferred. On this basis, the aqueous systems preferably may contain about 0.1–5% by weight of the copolymer component (polymer solids basis) and about 0.1 to about 10% by weight of the clay mineral, more preferably about 0.5–2.5% by weight of the copolymer and about 1–5% by weight of the clay mineral.

Depending on the end uses of the aqueous dispersions thickened or gelled in accordance with the invention, the aqueous dispersions may contain various ingredients of an active or inactive nature. For example, there may be added to the aqueous dispersions one or more of the following: perfume oils, dyes, evaporation retardants such as cetyl alcohol, abrasives such as silica and calcium carbonate, weighting agents such as barite, oils, emollients and preservatives. Low levels of surfactants may also be added. In some cases the surfactants further enhance thickening, elasticity and other properties, but can also detract from certain desirable properties, such as resistance of gelled compositions to crumbling. The surfactants which may be used include nonionics and anionics, singly or in combination, the selection necessarily depending upon compatibility with other ingredients of the thickened or thickenable dispersions of the invention. Cationic and amphoteric surfactants may also be used provided they are compatible with the copolymer and other ingredients of the aqueous system, or are used in such small amounts as not to cause incompatibility. A suitable amount of surfactant is about 0.01 to 5 parts by weight per part of copolymer or, on the basis of an aqueous system containing about 0.1 to 5% by weight of copolymer solids, about 0.1 to 1.0% by weight of surfactant. Amounts of surfactant can be varied outside these ranges depending on the type of copolymer and surfactant and the end use of the aqueous system in which they are present.

Suitable anionic surfactants that may be used include the higher fatty alcohol sulfates such as the sodium or potassium salt of the sulfates of alcohols having from 8 to 18 carbon atoms, alkali metal salts or amine salts of higher fatty acid having 8 to 18 carbon atoms, and sulfonated alkyl aryl compounds such as sodium dodecyl benzene sulfonate. Examples of nonionic surfactants include alkylphenoxypolyethoxyethanols having alkyl groups of aabout 7 to 18 carbon atoms and about 9 to 40 or more oxyethylene units such as octylphenoxypolyethoxyethanols, dodecylphenoxypolyethoxyethanols; ethylene oxide derivatives of long-chain carboxylic acids, such as lauric, myristic, palmitic, oleic; ethylene oxide condensates of long-chain alcohols such as lauryl or cetyl alcohol, and the like.

Examples of cationic surfactants include lauryl pyridinium chloride, octylbenzyltrimethylammonium chloride, dodecyltrimethylammonium chloride, condensates of primary fatty amines and ethylene oxide, and the like. Amphoteric surfactants include quaternary amine derivatives of fatty acids, such as the "Miranol" (trademark) surfactants.

The foregoing and other useful ionic, nonionic and amphoteric surfactants are described in the literature, such as "McCutcheon's Detergents & Emulsifiers 1978 Annual, North America Edition," MC Publishing Co., Glen Rock, N.J. 07452 U.S.A.

The following examples wherein all parts and percentages are by weight and degrees are Celsius, unless otherwise indicated, further illustrate the invention.

EXAMPLE 1

(A) Preparation of Methacrylic Acid Copolymer

An emulsion of monomers in water was prepared by mixing 118 g of ethyl acrylate, 23.6 g of stearyloxypoly(ethyleneoxy)$_{20}$ethyl methacrylate (monomer No. 8 of Table A above), 94.5 g of methacrylic acid, 6.3 g of 28% solution of sodium lauryl sulfate, and 271 g of water. To a reaction vessel containing 206 g of water and 6.3 g of 28% solution of sodium lauryl sulfate at 85° C. was added 5% of the monomer emulsion and 20.3 g of 1.25% aqueous ammonium persulfate. Ten minutes later, the remaining monomer emulsion and 817 g of 1.25% ammonium persulfate were gradually added over a period of one hour. The temperature of the mixture was maintained at 84°–86° C. After completion of monomer and initiator feed, the mixture was held at 85° C. for 15 min. and then 30 g of 0.3% ammonium persulfate solution was added. After another 15 min. hold at 85° C., the mixture was cooled and filtered. The filtrate gave an approximately 30% solids emulsion copolymer dispersion (essentially 100% yield) in which the copolymer composition is 10% stearyloxypoly(ethyleneoxy)$_{20}$ethyl methacrylate, 50% ethyl acrylate, and 40% methacrylic acid.

(B) Preparation of Aqueous Gel

The following components were separately prepared:
(1) 4.2 parts of 30% polymer emulsion of Part A in 31.7 parts of deionized (DI) water.
(2) 2.5 parts of bentonite clay added to 60 parts of DI water and stirred for two hours to disperse and hydrate the clay.

Components (1) and (2) were then blended and 1.6 parts of 10% NaOH added (0.7 equivalents based on carboxylic acid content of emulsion copolymer) to neutralize and solubilize the copolymer, and the dispersion was stirred. The resulting gel had a gel strength of 62 grams (see Table III footnote (1), for test procedure), was self-supporting over a temperature range of 0°–50° C., and showed no syneresis after three freeze-thaw cycles. When suitable amounts of color and perfume are added to the aqueous blend of components (1) and (2) prior to neutralization, the resulting gel is useful as an air freshener.

EXAMPLE 2

A series of aqueous dispersions was prepared from components 1 and 2 of Example 1B, differing in the total solids content of methacrylic acid copolymer and bentonite clay, and the dispersions were neutralized with NaOH substantially as described in Example 1B. The viscosities of the dispersions were compared at various solids levels with the results set forth in Table I. The Table includes a comparison with an ethyl acrylate-methacrylic acid copolymer (EA/MAA) having a 60/40 monomer composition and prepared substantially in accordance with the procedure of Example 1(A), including neutralization with NaOH as in Example 1B. Polymers of this type are described in British Pat. No. 870,994, specifically Table I, page 8, line 11 thereof.

The data of Table I below shows a synergistic increase in thickening upon admixture of the methacrylic acid copolymer of the invention with the bentonite clay, and neutralization. Furthermore, the data shows thickening activity even at low concentrations of the components (e.g., 0.14% polymer and 0.1% clay) and significantly less thickening when the EA/MAA copolymer is used in place of the copolymer of the invention.

TABLE I

| Copolymer | % Polymers Solids | Viscosity[1] (cps) % Bentonite Clay | | | | |
|---|---|---|---|---|---|---|
| | | 0 | 0.1 | 1 | 3 | 5 |
| None | 0 | | 1 | 170 | 275 | 350 |
| Example 1A | 0.14 | 50 | 110 | 7,000 | | |
| Example 1A | 0.25 | 1,100 | | 19,000 | | |
| Example 1A | 0.5 | 30,000 | | 140,000 | 210,000 | |
| Example 1A | 1.0 | 450,000 | | 700,000 | 1,400,000 | 2,300,000 |
| EA/MAA, 60/40 | 0.25 | 220 | | 290 | | |
| EA/MAA, 60/40 | 0.5 | 5,500 | | 19,500 | | |

[1]Brookfield Viscometer, 0.5 rpm, 75° F.

EXAMPLE 3

Aqueous dispersions were prepared substantially as described in Examples 1B and 2 except for substitution for the bentonite of "Veegum" clay, a Mg-Al silicate of higher Mg content than bentonite and believed to be a saponite species of the montmorillonite group of clay minerals. As shown in Table II this blend also exhibits synergistic thickening.

TABLE II

| Copolymer | % Polymers Solids | Viscosity[1] (cps) % Veegum[2] Clay | | |
|---|---|---|---|---|
| | | 0 | 1 | 3 |
| None | 0 | | 1 | 240 | 3,600 |
| Example 1A | 0.5 | 30,000 | 58,000 | 380,000 |

[1]Brookfield Viscometer, 0.5 rpm, 75° F.
[2]Trademark, R. T. Vanderbilt Co.

EXAMPLE 4

Aqueous gels of the methacrylic acid copolymers of Example 1A and inorganic powders were prepared and neutralized as in Example 1B and compared for gel strength. The results are shown in Table III. It will be noted that the copolymer without clay provides gels having low strength, and that the non-swelling clays, talc, silica and alumina provided little or no improvement in gel strength, as compared with the high gel strength resulting from admixture of the copolymer with the bentonite and Mg-Al clays. Clay alone (without the copolymer) at 2% solids or less (and even up to about 8%) will not gel an aqueous system.

TABLE III

| % Solids of Example 1A Copolymer | Additive | Gel Strength[1] (g) % Additive Solids | | |
|---|---|---|---|---|
| | | 0 | 1.7 | 2.0 |
| 1 | none | 5 | | |
| 2 | none | 8 | | |
| 3 | none | 14 | | |
| 0 | Bentonite Clay[2] | | 0 | 0 |
| 2 | Bentonite Clay[2] | | 44 | 55 |
| 2 | Bentonite Clay[3] | | 36 | |
| 2 | Mg—Al Silicate[4] | | | 65 |
| 2 | Kaolin Clay - Aluminum Silicate Clay | | | 13 |
| 2 | Hydrated Na Alumino silicate[8] | | | 17 |
| 2 | Diatomaceous Earth[5] | | | 13 |
| 2 | Talc - Magnesium Silicate | | | 13 |
| 2 | Alumina | | | 16 |
| 2 | Colloidal Silica[6] | | | 19 |
| 2 | Colloidal Silica[7] | | | 27 |

[1]grams weight to force a 2 cm[2] cylinder a distance of 0.4 cm. into the gel.
[2]"Macogel" (trademark), Dresser Industries.
[3]"Hydrogel" (trademark), Wyo-Ben Products Inc.
[4]"Veegum" (trademark), R. T. Vanderbilt Company.
[5]"Celite" (trademark) 499, Johns-Manville Corporation.
[6]"Ludox LS" (trademark), DuPont Company.
[7]"Cab-O-Sil" (trademark) M-5, Cabot Corporation.
[8]"Zeolex" (trademark) 23, J. M. Huber Corporation.

EXAMPLE 5

The copolymer of Example 1A, bentonite clay and NaOH in the ratio 0.5/1/0.1 parts are slurried in 98.4 parts of water and pressure filtered to force out the unbound water. The resulting filter cake holds 41 parts of water per 1 part of solids. Bentonite clay alone, after similar treatment, holds only 3 parts of water. The neutralized copolymer solution alone (without clay) passes through the filter (or other porous medium). These results demonstrate the ability of the combination to adsorb and immobilize an appreciable quantity of water, thus making it useful as an absorbent for aqueous fluids, for example as a dry impregnant for diapers, tampons and the like.

EXAMPLE 6

An emulsion copolymer was prepared essentially as described in Example 1A except that the monomer composition was alkoxy (mixture of $C_{22}$ to $C_{26}$) poly(ethyleneoxy)$_{33}$ethyl methacrylate, ethyl acrylate, and methacrylic acid in the weight ratio 5/55/40. The copolymer was blended with bentonite clay and cetyl alcohol in water and neutralized, in the following proportions:

| copolymer | 1.5% polymer solids |
|---|---|
| clay | 2.5% |
| NaOH | 0.7% |
| cetyl alcohol | 1.0% |
| water | balance to make 100% |

The result was a firm gel which provided gel strength (measured as in Example 3, Table III) of 130 as compared with a gel strength of 78 for a gel prepared from the same blend but using the copolymer of Example 1A in place of the copolymer of this Example.

EXAMPLE 7

A liquid abrasive cleaner is made by blending the following ingredients in the order listed:

```
36.18 parts water
   50 parts calcium carbonate
 1.67 parts of 30% polymer emulsion of Example 1A
 6.25 parts of an 8% dispersion of bentonite clay
      in water
  2.5 parts sodium tripolyphosphate
  2.5 parts "Triton" (trademark) X-102 nonionic
      surfactant
  0.9 parts of 10% sodium hydroxide.
```

The abrasive cleaner does not separate on standing and has a viscosity of 5500 cps. at 0.5 rpm.

EXAMPLE 8

A smooth hand cream which is easily incorporated into the skin without leaving an oily residue and having a viscosity of 1,200,000 cps (at 0.5 rpm) is made with the following formulation:

| Part A | Part B |
|---|---|
| 67.75 parts water | 2 parts mineral oil |
| 12 parts glycerine | 10 parts cetyl alcohol |
| 1 part of 30% polymer emulsion of Ex. 1A | 0.5 parts "Ethomeen" (trademark) C-25[1] |
| 6.25 parts of an 8% dispersion of bentonite clay in water | |
| 0.5 parts triethanolamine | |

[1]Armak Chemicals

Parts A and B are heated to 75° C. The Part B composition is then added to Part A with vigorous stirring and the mixture is quickly cooled to 30° C.

I claim:
1. As a thickening agent for aqueous systems, a composition comprising a mixture of:
(A) a water swellable clay mineral, and

(B) a water insoluble emulsion polymer, an aqueous dispersion of which will thicken upon addition of a neutralization agent, of
(1) 20-50 wt. % of (meth)acrylic acid,
(2) 0.5-25 wt. % of at least one monomer of the formula (I):

$$H_2C=C(R)-C(O)-O-(CH_2CH_2O)_n-R^o$$

wherein R is H or $CH_3$, n is at least 2 and has an average value up to 60 or more, and $R^o$ is a group having at least 8 carbon atoms selected from alkyl, alkaryl and polycyclic hydrocarbyl,
(3) at least 30 wt. % of an alkyl (meth)acrylate wherein the alkyl group has 1 to 4 carbon atoms, and
(4) zero to 1.0 wt. % of a polyethylenically unsaturated monomer;

the proportions of (A) and (B) being effective, upon addition of a neutralizing agent for (B), for thickening an aqueous dispersion formed therewith.

2. A composition as in claim 1 wherein the proportions of (A) and (B) are effective for forming a firm gel upon at least partial neutralization and admixture with water.

3. A composition as in claim 1 wherein (A) is a montmorillonite clay mineral.

4. A composition as in claim 1 wherein (B) is a copolymer of
(1) 30-45 wt. % of (meth)acrylic acid,
(2) 1-15 wt. % of said monomer of formula (I), wherein $R^o$ contains about 8 to 24 carbon atoms, and
(3) about 40-60 wt. % of said alkyl (meth)acrylate.

5. A composition as in claim 1 or 4 wherein said monomer (2) is

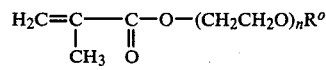

wherein $R^o$ is an alkyl group having 12-18 carbon atoms, and n has an average value of at least about 10.

6. A composition as in claim 1 wherein (B) is a copolymer of
(1) 30-45 wt. % of methacrylic acid,
(2) 1-15 wt. % of said monomer of formula (I) wherein n has an average value of about 10-60 and $R^o$ is alkyl having 12-18 carbon atoms, and
(3) 40-60 wt. % of ethyl acrylate.

7. A composition as in claim 1 wherein the amount of (A) is about 0.1-10 parts by weight and the amount of (B) is about 0.1-5 parts by weight, and (A) is a montmorillonite clay mineral.

8. A composition comprising an aqueous dispersion thickened with effective amounts of an at least partially neutralized composition of claim 1, 4, 6 or 7.

9. A composition comprising an aqueous gel prepared by dispersing in water and at least partially neutralizing the composition of claim 2.

10. A method of thickening an aqueous dispersion, comprising blending therewith a composition as in claim 1, 4, 6 or 7, and at least partially neutralizing said composition before, after or simultaneously with said blending.

11. A method of forming an aqueous gel, comprising dispersing in water the composition of claim 7 and at least partially neutralizing said composition before, after or during said dispersing.

* * * * *